(12) United States Patent
Jang

(10) Patent No.: US 6,758,803 B2
(45) Date of Patent: Jul. 6, 2004

(54) AUTOMATED CENTRIFUGE SYSTEM FOR AUTOMATICALLY CENTRIFUGING LIQUIDS CONTAINING BIOLOGICAL MATERIALS

(75) Inventor: Gi Young Jang, Seoul (KR)

(73) Assignee: Bionex, Inc., Seoul ( * ) Notice: Subject to any disclaimer, the term of this patent is extended or adjusted under 35 U.S.C. 154(b) by 0 days.

(21) Appl. No.: 10/188,453

(22) Filed: Jul. 3, 2002

(65) Prior Publication Data

US 2004/0002415 A1 Jan. 1, 2004

(30) Foreign Application Priority Data

Jun. 28, 2002 (KR) .............................. 10-2002-0036642

(51) Int. Cl.[7] .......................... B04B 5/02; B04B 13/00
(52) U.S. Cl. .............................. 494/10; 494/16; 494/20
(58) Field of Search ................................ 494/1, 10, 11, 494/12, 16, 20, 45; 422/72; 74/572

(56) References Cited

U.S. PATENT DOCUMENTS

| | | | | |
|---|---|---|---|---|
| 3,151,073 A | * | 9/1964 | Anthon | .......................... 494/1 |
| 4,927,545 A | * | 5/1990 | Roginski | .................... 210/745 |
| 5,166,889 A | * | 11/1992 | Cloyd | .......................... 702/22 |
| 5,681,530 A | | 10/1997 | Kuster et al. | |
| 5,730,697 A | * | 3/1998 | Auchinleck | .................. 494/20 |
| 5,769,775 A | | 6/1998 | Quinlan et al. | |
| 6,060,022 A | | 5/2000 | Pang et al. | |
| 6,196,961 B1 | * | 3/2001 | Hoshiba et al. | ................ 494/14 |
| 6,589,789 B1 | * | 7/2003 | Hubert et al. | ................. 422/72 |

FOREIGN PATENT DOCUMENTS

| | | | |
|---|---|---|---|
| EP | 0569115 A2 | * | 11/1993 |
| FR | 2629370 | * | 10/1989 |
| JP | 4-242168 | * | 8/1992 |
| JP | 8-108099 | * | 4/1996 |
| JP | 11-276933 | * | 10/1999 |

* cited by examiner

*Primary Examiner*—Charles E. Cooley
(74) *Attorney, Agent, or Firm*—Blakely Sokoloff Taylor & Zafman

(57) ABSTRACT

An automated centrifuge system. The centrifuge includes a rotor in which at least two swing buckets with at least two microplates mounted thereon are provided, a multi-joint robot with at least three joints which includes a gripper attached to a final arm thereof and a finger attached to the gripper, and a controller for controlling the predetermined procedures and operation of the robot. The centrifuge and multi-joint robot are disposed close to each other on a rigid bottom plate. A sensor for use in position detection is attached to the gripper or finger. At least one marker is attached at a predetermined position on a central frame of the rotor.

20 Claims, 7 Drawing Sheets

AUTOMATED CENTRIFUGE SYSTEM FOR AUTOMATICALLY CENTRIFUGING LIQUIDS CONTAINING BIOLOGICAL MATERIALS

BACKGROUND OF THE INVENTION

1. Field of the Invention

The present invention relates to an automated centrifuge system, and more particularly, to an automated centrifuge system for automatically centrifuging liquids containing biological materials such as nucleic acids using a conventional centrifuge.

2. Description of the Prior Art

Centrifugation is a typical technique most frequently used in experiments in the fields of biology and medicine, and a centrifuge is utilized in almost all biological laboratories.

The centrifuge is a machine for performing separation, purification and concentration of biological materials having different ingredients or specific gravities, which are included in test tubes, under the action of centrifugal force generated by rotation of a rotor mounted with the test tubes. The centrifuge is used to separate liquids having different specific gravities from one another or solid particles from the liquids containing the particles. Performance of the centrifuge is determined based on a ratio of a centrifugal force to a gravitational force, which is called a centrifugal effect. That is, the centrifugal effect is expressed as (centrifugal acceleration)/(acceleration of gravity). Since magnitude of the centrifugal force is defined as (mass)×(radius of rotation)×(square of angular velocity), the centrifugal effect is determined according to a rotational speed and radius of rotation of the centrifuge. Further, the centrifuge is categorized into the following three types according to the centrifuge speed: a low speed centrifuge of which rotational speed is lower than 100 rpm, a high speed centrifuge of which rotational speed is around 10,000 rpm, and an ultra-high speed centrifuge of which rotational speed is greater than 100,000 rpm.

As equipment for completely automating a centrifuging operation using any one of various centrifuges, some equipment such as AutoGeneprep 960 available from Autogen, Inc. in Framingham, Mass., U.S.A. and Genesis available from Tecan Group AG in Maennedorf, Switzerland have been brought into the market. However, the equipment is very restrictive in that some specific centrifuges, liquid handlers for exclusive use in the specific centrifuges, and robots must be placed onto respective desired positions which manufacturers of the automated equipment have already determined. Further, test tubes or microplates specified by the manufacturers should be utilized. Thus, an arbitrary centrifuge hardly can be used. Therefore, there are problems in that it is difficult to use the automated equipment for a specific purpose a user wishes to achieve and the equipment cannot be used together with a novel machine such as a newly developed liquid handler.

Furthermore, the following characteristics of centrifugation make it difficult to develop an automated centrifuge system in which a general centrifuge and general devices related thereto are used. That is, since angular positions of the rotor mounted with the test tubes including samples, which will be centrifuged or have been already centrifuged, are random before start of or after completion of the centrifugation, position information on placement of the respective samples cannot be easily obtained. In addition, in a case where a protective cover for preventing inadvertent outflow of the samples is further provided at the rotor mounted with the test tubes including the samples therein, an operation of automatically opening and closing the protective cover makes automation of the centrifugation still more difficult.

Moreover, in a field of the automation industry for recognizing a target object placed on an arbitrary position, a fixed vision camera is generally installed above the target object so as to determine the position of the target object. However, the vision camera is expensive and has difficulty in performing three-dimensional measurement. Further, complex vision software, a computer, and the like would be required. Therefore, it is not adequate for experiments in a laboratory or processing of a small quantity of samples.

In the meantime, in a case where the centrifugation is performed using the microplate or some types of test tubes, the centrifuge other than the ultra-high speed centrifuge of which rotational speed is greater than 100,000 rpm is generally used. Thus, rotational balance of the centrifuge is not critical. Further, the protective cover for preventing the outflow of the samples is not provided in such a case. Therefore, the automated operation related to the opening and closing of the protective cover can be negligible.

SUMMARY OF THE INVENTION

The present invention is contemplated to solve the above problems in the prior art.

In particular, the present invention places great importance on automation of a process of recognizing the positions of microplates or test tubes before start or after completion of centrifugation, which was a major obstacle to an automated centrifugation, when a multi-joint robot and a general centrifuge are used together in a state where they are disposed close to each other. That is, the present invention is characterized by a process of automatically recognizing the positions of the test tubes in tube holes of a rotor of the centrifuge or the microplates in swing buckets connected to the rotor so as to correctly handle the microplates or the test tubes.

Further, the present invention performs automated centrifugation through a process of recognizing correct positions of the test tubes, the microplates or the like by using inexpensive optical fiber photoelectric sensor or laser displacement measurement sensor instead of the vision camera which is expensive and of which control is complicated.

Accordingly, an object of the present invention is to provide an automated centrifuge system by which a process of centrifuging samples can be automatically performed in a general centrifuge by automatically and more efficiently determining positions of test tubes or microplates in the general centrifuge using combination of a general laser displacement measurement sensor or optical sensor and a relevant marker and a multi-joint robot with at least three joints.

According to an aspect of the present invention for achieving the above objects, there is provided an automated centrifuge system for automatically centrifuging liquids containing biological materials such as nucleic acids in accordance with predetermined procedures, comprising: a centrifuge including a rotor in which at least two swing buckets with at least two microplates mounted thereon are provided so as to perform centrifugation of the liquids, a multi-joint robot with at least three joints which includes a gripper attached to a final arm thereof and fingers attached to the gripper, and a controller for controlling the predetermined procedures and the operation of the robot.

Furthermore, the centrifuge and the multijoint robot are disposed close to each other on a rigid bottom plate; a position detection sensor is attached to the gripper or one for fingers, at least one marker is attached at a predetermined position on a central frame of the rotor, the predetermined position is spaced apart from a rotating shaft of the rotor by a predetermined radial distance; and the controller causes the gripper to be moved so that the sensor is placed onto a circumference of a circle having a radius equal to the predetermined radial distance and the gripper to be moved around an axis of the rotating shaft of the rotor so that the sensor can detect a position of the marker, thereby automatically performing the predetermined procedures through the detection of positions of the microplates mounted to the swing buckets of the centrifuge.

According to another aspect of the present invention, there is also provided An automated centrifuge system for automatically centrifuging liquids containing biological materials such as nucleic acids in accordance with predetermined procedures, comprising: a centrifuge including a rotor in which a plurality of tube holes for receiving a plurality of test tubes with the liquids contained therein are formed at an equiangular interval on a circumference of a circle having a predetermined radius from a rotating shaft of the rotor, a multi-joint robot with at least three joints which includes a gripper attached to a final arm thereof and a finger attached to the gripper, and a controller for controlling the predetermined procedures and the operation of the robot. Furthermore, the centrifuge and the multi-joint robot are disposed close to each other on a rigid bottom plate; a sensor for use in position detection is attached to the gripper or finger, at least one marker is attached at a predetermined position on a central frame of the rotor, the predetermined position is spaced apart from a rotating shaft by a predetermined radial distance smaller than the predetermined radius; and the controller causes the gripper to be moved so that the sensor is placed onto a circumference of a circle having a radius equal to the predetermined radial distance and the gripper to be moved around an axis of the rotating shaft of the rotor so that the sensor can detect a position of the marker, thereby automatically performing the predetermined procedures through the detection of positions of the respective test tubes inserted into the tube holes of the rotor of the centrifuge.

BRIEF DESCRIPTION OF THE DRAWINGS

The above and other objects and features of the present invention will become apparent from the following description of preferred embodiments given in connection with the accompanying drawings, in which.

DETAILED DESCRIPTION OF THE INVENTION

Hereinafter, automated centrifuge systems according to preferred embodiments of the present invention will be explained in detail with reference to the accompanying drawings.

Figure 1:
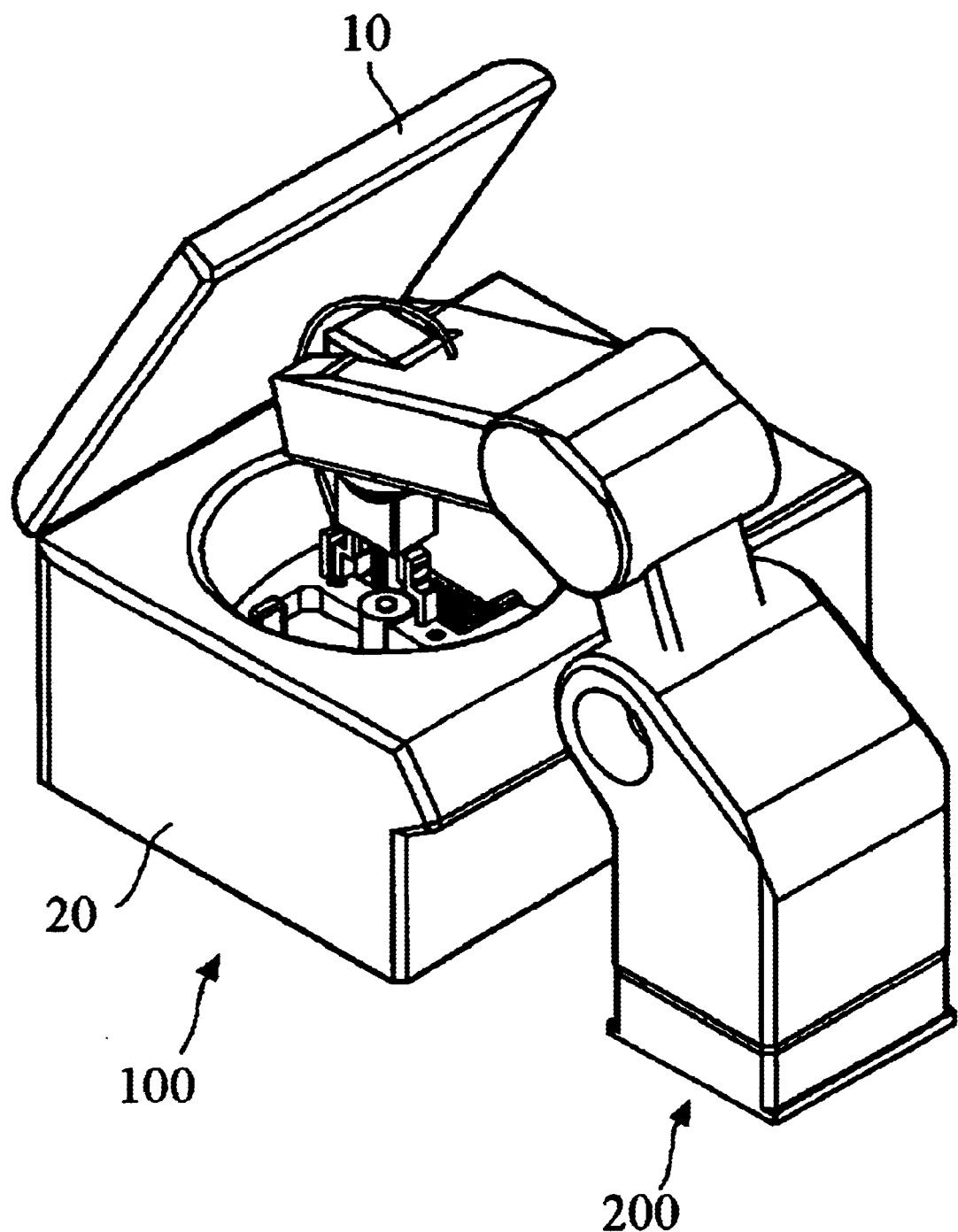
FIG. 1 is a perspective view schematically showing the constitution of an automated centrifuge system according to an embodiment of the present invention.
Figure 2:
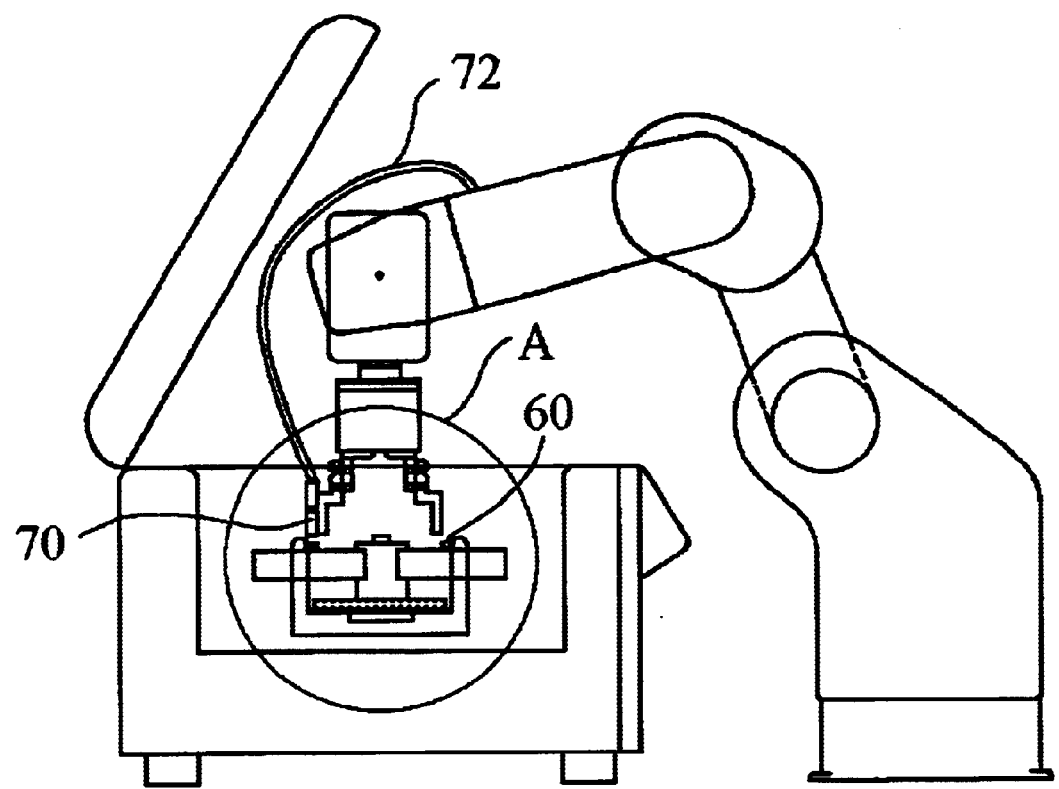
FIG. 2 is a side view of the automated centrifuge system shown in FIG. 1.
Figure 3:
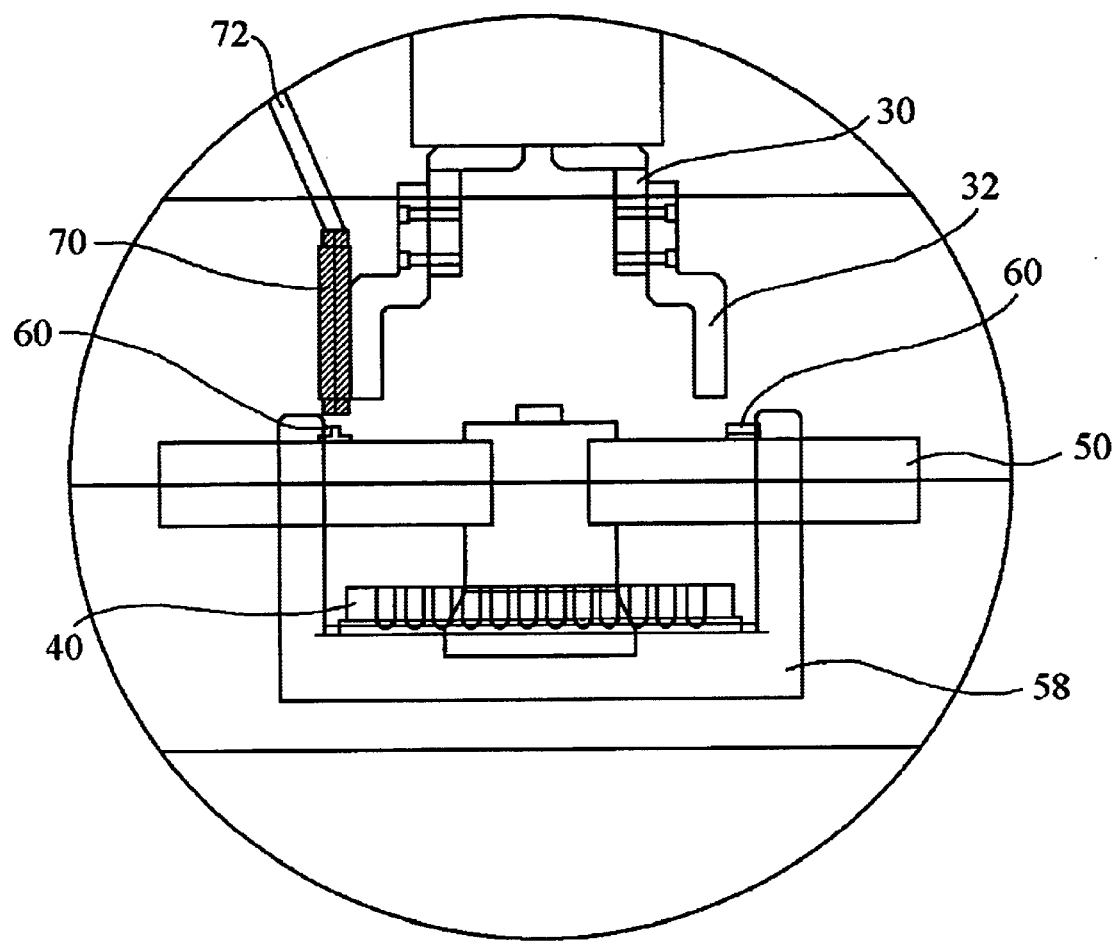
FIG. 3 is an enlarged sectional view of a portion shown in a circle A of FIG. 2.
Figure 4:
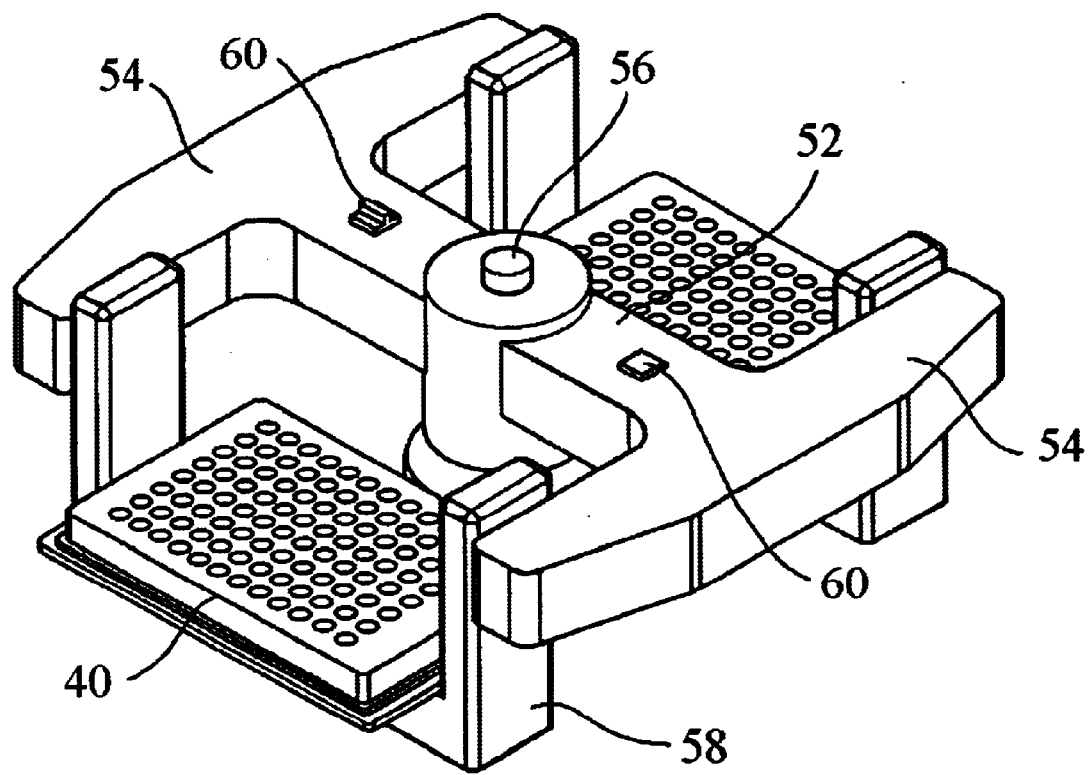
FIG. 4 is a perspective view showing how a rotor, microplates mounted in the rotor, and a marker attached onto a frame of the rotor are arranged with respect to one another within a centrifuge shown in FIG. 1.
Figure 5:
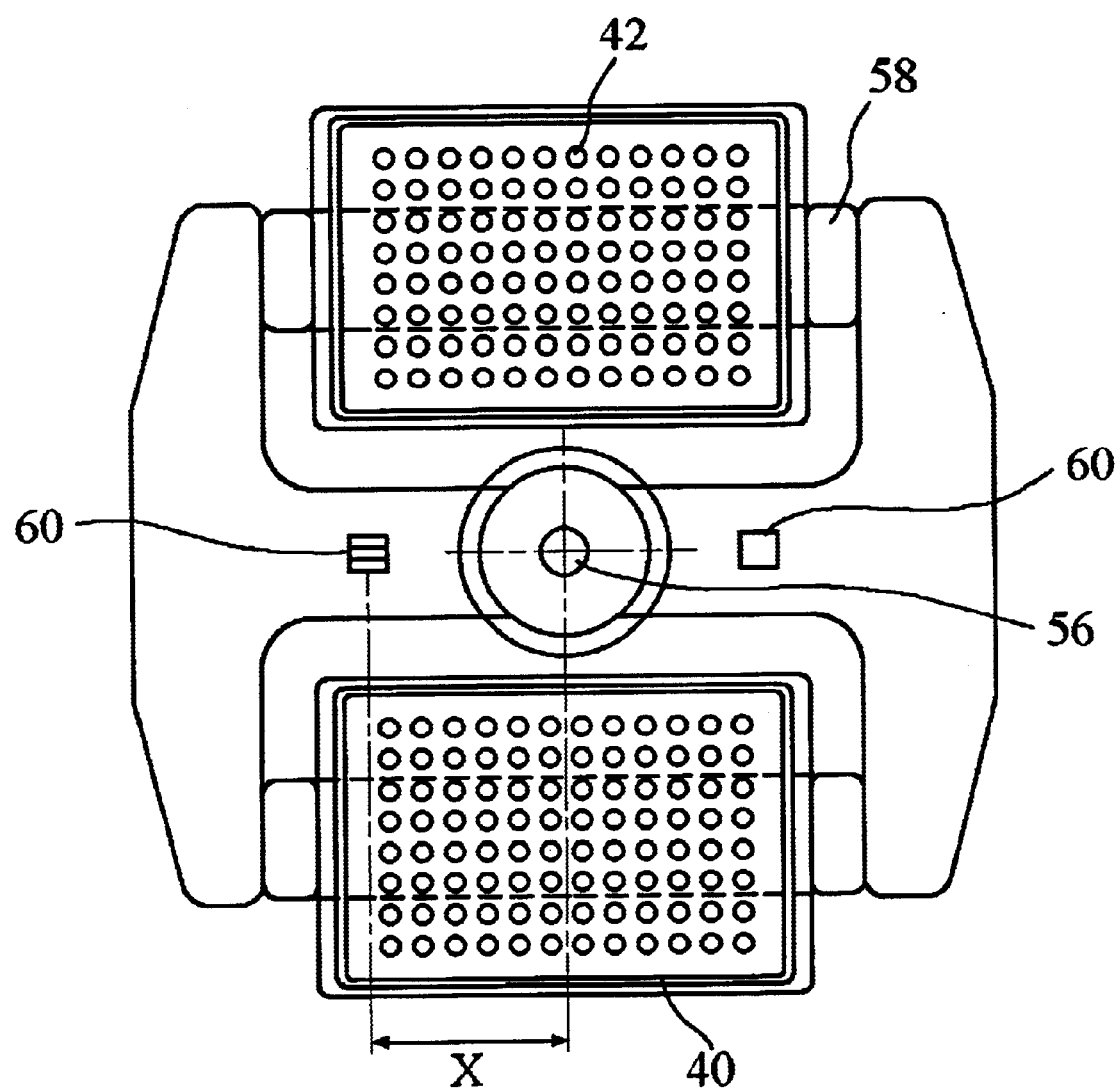
FIG. 5 is a plan view of FIG. 4.

FIG. 1 is a perspective view of an automated centrifuge system according to an embodiment of the present invention, which comprises a general centrifuge for performing centrifugation using microplates and a multi-joint robot used to mount and demount the microplates into and from the centrifuge. FIG. 2 is a side view of the automated centrifuge system shown in FIG. 1. FIG. 3 is an enlarged sectional view of a portion shown in a circle A of FIG. 2. FIG. 4 is a perspective view showing an arrangement of a rotor, microplates mounted in the rotor, and a marker attached onto a frame of the rotor with respect to one another within a centrifuge shown in FIG. 1. FIG. 5 is a plan view of FIG. 4.

Referring to FIGS. 1 to 3, the automated centrifuge system of the present invention comprises a general centrifuge 100 and a multi-joint robot 200 which are placed close to each other at predetermined positions onto a rigid and flat bottom plate (not shown), and a controller (not shown) for controlling the operation of the robot. Here, the centrifuge 100 is a conventional centrifuge commonly used in laboratories and the like. It is preferred that the multi-joint robot 200 be a robot with at least three joints.

In general, the centrifuge 100 comprises a cover 10 and a main body 20. The cover 10 is opened and closed before and after centrifugation, and can be easily and automatically opened and closed using the conventional multi-joint robot. An upward open space having a suitable size, in which a rotor 50 of the centrifuge is installed, is formed in the main body 20. As well shown in FIGS. 4 and 5, the rotor 50 includes a rotating shaft 56, and a rotor frame 52, 54 extending radially outward from the rotating shaft 56. The rotor frame is composed of a central frame 52 extending radially outward from the rotating shaft 56 and a peripheral frame 54 extending by a predetermined length in a direction perpendicular to the length of the central frame from an outer end of the central frame. Microplates 40 for holding samples containing biological materials such as nucleic acids to be centrifuged are installed to the rotor 50 by using swing buckets 58 which are mounted into recessed portions defined by the central and peripheral frames 52, 54. After the microplates 40 have been mounted to the rotor 50 in such a manner, the cover 10 is closed and the centrifugation operation of the centrifuge 100 is started. Then, as the rotor 50 is rotated about the rotating shaft 56, the swing buckets 58 mounted with the microplates 40 are swung or pivoted to face an inner wall of the main body of the centrifuge. Accordingly, the samples in respective wells of the microplates 40 are centrifuged.

In the meantime, in order to perform a function of opening and closing the cover 10 of the centrifuge and to automatically mount and demount the microplates or test tubes into and from the centrifuge by detecting the positions of the microplates or test tubes, the multi-joint robot 200 with at least three joints is utilized. Well known in the art, the robot 200 is composed of a plurality of arms and a plurality of joints for connecting the multiple arms. As well shown in FIG. 3, is a gripper 30 attached to an end of a final arm of the robot. The gripper 30 is used to grip a predetermined target object, and may be used in a state where fingers 32 are further attached to an end of the gripper 30, if desired.

Hereinafter, unique features for performing a process of detecting the positions of the microplates and/or test tubes according to the present invention, which are essential for performing automated centrifugation using the conventional centrifuge 100 and the multi-joint robot 200 with at least three joints, will be explained in detail.

Referring again to FIG. 3, a sensor 70 is mounted to one of the fingers 32 attached to the gripper 30 of the robot 200. The sensor 70 is used for detecting the positions of the microplates or test tubes which are mounted to the rotor 50 of the centrifuge 100, as described later. A radius of rotation of the robot 200, i.e. a range of motion of the robot, is approximately within 100 cm, and may be about 50 cm, if desired. In particular, the robot of the present invention includes a signal cable 72 which is connected to the sensor 70 for receiving position information of the microplates or tubes from the sensor 70 mounted to the finger 32.

As shown in FIGS. 3 to 5, two markers 60 are attached at predetermined positions on the central frame 52 of the rotor 50 of the centrifuge 100. The markers 60 may have proper numbers, shapes and sizes according to kinds of the sensor 70 to be explained later in detail.

Two or more markers 60 may be disposed in order to reduce a scanning time or to detect the positions of a plurality of microplates or test tubes. In such a case, the markers are preferably disposed at equiangular positions spaced apart an angular interval, i.e. an angle obtained by dividing 360 degrees by the number of markers. Further, in order not to exert an influence on the balance of the centrifuge, the markers preferably have equal or similar weights.

In addition, the markers 60 may have various configurations according to the kind of the sensor 70. For example, in case of a laser displacement measurement sensor (e.g., laser sensor), a small rectangular plate-like marker 60 having a predetermined thickness and/or a small rectangular plate-like marker 60 having an inverse T shape with a central portion thereof protruding slightly upward can be used. When the sensor 70 passes over the marker 60 while scanning the marker along a circumference of a circle having a predetermined radius, which is centered on the rotating shaft, on the central frame of the rotor of the centrifuge, the sensor can detect any differences in displacement (measured distance) resulting from the predetermined thickness of the marker. In particular, when the sensor passes over the marker having a central protruding portion, the displacement difference is detected more remarkably, and thus, the positions of the markers can be more easily detected. As far as such a displacement difference can be detected, round or any other shaped plate-like markers may be used instead of the rectangular plate-like markers.

On the other hand, in a case where the photoelectric sensor having a color-discriminating function is used, it is possible to utilize rectangular markers which are very thin to an extent that the thickness can be negligible and have predetermined colors clearly distinguishable from that of the central frame of the rotor and easily detectable by the sensor. The color-discriminating sensors can obtain specific signal values whenever it passes over the markers having the predetermined colors. Such a sensor is advantageous in that it does not exert any influence on the rotating balance of the rotor of the centrifuge upon rotation thereof.

Furthermore, in a case where a centrifuge having a cooling or heating function is used, moisture or heat may exist in or be added to an environment around the rotor. Thus, it is preferred that the markers be made of materials which cannot be affected by the water or moisture and cannot be contracted or expanded by temperature change so that they can be efficiently used even in the wet or heated environment. For example, the marker 60 may be made of plastic, aluminum or the like, and coated paper, if desired.

Hereinafter, the sensor for detecting the positions of the microplates or test tubes using these markers will be explained.

Distance measuring laser sensors (laser sensors) are generally used in connection with the small rectangular plate-like marker having a predetermined thickness. Since the laser sensors use light as a medium, the laser sensors are advantageous in that they can perform high speed measurement and are hardly influenced by environmental factors such as temperature and moisture. The laser sensors are divided into three types: interferometry, optical triangulation and time of flight, according to measurement methods. According to the optical triangulation method, a distance between the sensor and the target object is calculated by using trigonometry based on positions where a laser beam irradiated to the target object is reflected to the sensor, and is suitable for a field where high precision is required even when the target object is spaced apart from the sensor by several centimeters or several meters. Thus, the optical triangulation type of laser sensor is generally employed in the present invention.

On the other hand, in a case where the marker having its own specific color is used, an optical fiber photoelectric sensor for detecting the existence and position of the target object using infrared rays, red light or green light is generally utilized. The optical fiber photoelectric sensor comprises an amplifier unit including a light-transmitting element, a light-receiving element and a signal processing circuit, and an optical fiber unit for transmitting light to the target object. Further, the optical fiber photoelectric sensor detects the position of the marker by transferring the light to the target object through a transmission fiber and detecting intensity of light that is transmitted through or reflected to the target object and then arrives at the light-receiving element of the amplifier unit through a receiving fiber. The optical fiber photoelectric sensor currently used has a measuring range of 5 cm to 2 m. In particular, the optical fiber photoelectric sensor having a function of recognizing the target object by intensity of reflected light, which varies according to a distance from and a color of the target object is employed in the present invention.

Hereinafter, the specific constitution and operation of the automated centrifuge system according to the present invention for automatically performing the centrifugation in the conventional centrifuge using the aforementioned sensor and markers will be described.

Referring again to FIGS. 1 to 5, the conventional centrifuge 100 and the multijoint robot 200 with at least three joints, which is mounted with the gripper, fingers and sensor, are disposed close to each other at predetermined positions on the rigid and flat bottom plate (not shown). The sensor 70, which is installed to the gripper 30 attached to the final arm of the robot or to one of the fingers 32 attached to the gripper 30, is used to detect the positions of the microplates or test tubes in cooperation with the marker 60.

It has been already described that the marker 60 may be either an inverse T-shaped marker having a protruding portion for use in displacement detection or a very thin marker for use in color detection. The marker 60 is attached at a position spaced apart by a predetermined distance X (i.e., 100 cm or less) from the rotating shaft 56 of the rotor 50 on the central frame 52 of the rotor. As well shown in FIGS. 4 and 5, it is preferred that two different types of markers 60 be disposed at the two predetermined positions. That is, in such a case, if the marker 60 attached at any one position is determined to designate the position of the microplate 40 placed at a position which is further displaced by 90 degrees in a predetermined rotating direction of the rotor of the centrifuge, the two positions of the microplates 40 can be correctly determined without any confusion. Even in a case where only one marker 60 is used, a plurality of positions of the microplates can also be correctly determined in the same manner as above. In the meantime, in the case where only one marker is used, the sensor 70 may scan the circumference of the circle having the radius X from the central shaft 56 of the rotor 50 up to maximum 360 degrees. However, in the case where n different markers are used, the sensor can scan the circumference of the circle having the radius X by at most 360/n degrees. Furthermore, in the case where only one marker is attached, the weight of the marker should be minimized so as not to exert an influence on the rotational balance of the centrifuge. For example, it is preferred that the weight of the marker be 10 grams or less.

In order to cause the sensor 70 to scan the circumference of the circle having the radius X from the rotating shaft 56 of the rotor 50, the gripper 30 of the robot 200 is moved as follows. That is, the gripper 30 can be moved toward or away from the centrifuge in a right and left direction in FIG. 3 under the control of a conventional robot controller (not shown). It is preferred that such a range of motion be 100 cm or less. More preferably, the range of motion is 50 cm or less. If the gripper is moved by a proper distance in consideration of the predetermined radius X and a positional relationship among the gripper 30, the fingers 32 attached to the gripper and the sensor 70 attached to one of the fingers, the center of the sensor 70 is correctly placed onto the circumference of the circle where the marker 60 is located. At this time, if the final arm of the robot is moved in the predetermined rotating direction, the sensor 70 detects the marker 60 while scanning the circumference of the circle having the radius X where the marker 60 is located. Thus, the positions of the microplates 40 mounted in the centrifuge 100 can be correctly detected. Then, signals acquired from the sensor during the scanning operation thereof are transmitted to the controller (not shown) through the signal cable 72.

Figure 6:
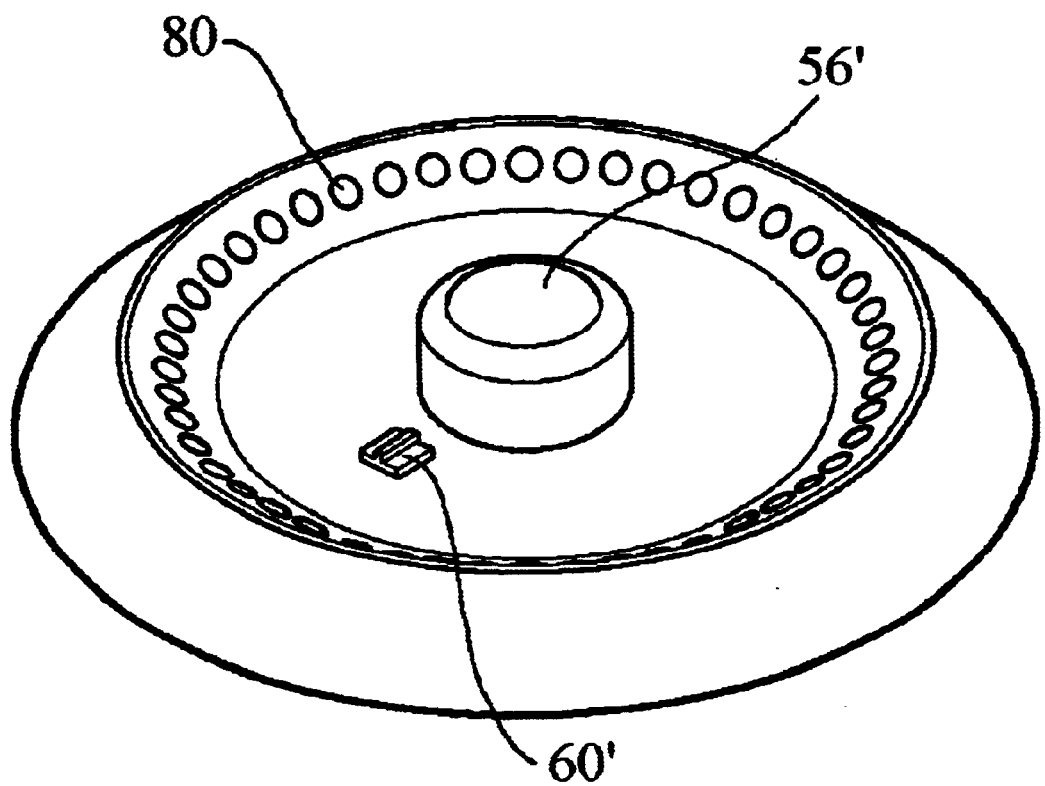
FIG. 6 is a perspective view showing an arrangement of a rotor of a centrifuge for performing centrifugation using test tubes and a marker attached onto an upper surface of the rotor according to another embodiment of the present invention.
Figure 7:
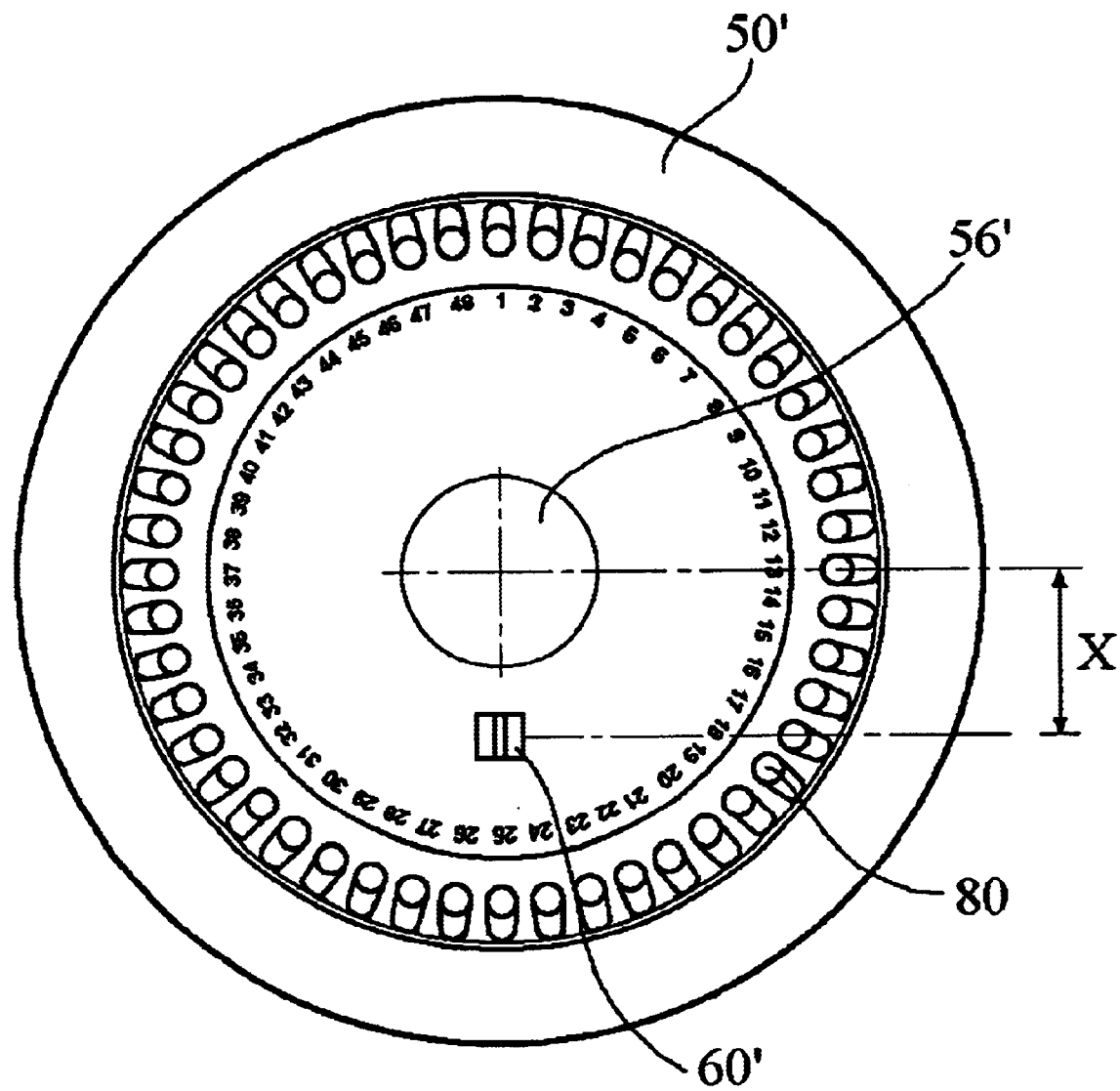
FIG. 7 is a plan view of FIG. 6.

FIG. 6 is a perspective view showing an arrangement of a rotor and a marker attached onto an upper surface of the rotor within a centrifuge for performing the centrifugation using test tubes instead of the microplates according to a second embodiment of the present invention, and FIG. 7 is a plan view of FIG. 6.

The centrifuge including another type of rotor 50' in which a plurality of tube holes for receiving a plurality of test tubes are formed instead of the swing buckets for receiving the microplates are used in the second embodiment of the present invention. The second embodiment is almost similar to the first embodiment in view of their constitutions and operations except their constitutions of the rotor. As shown in FIGS. 6 and 7, the rotor 50' according to the second embodiment of the present invention is provided with a rotating shaft 56' at the center thereof, and is formed with a plurality of tube holes 80 on a circumference of a circle having a predetermined radius in an annular inclined surface outside of an upper flat surface of the rotor. It is understood that the tube holes 80 are formed in the inclined surface of the rotor 50' so as to centrifuge the samples in the test tubes.

Similarly to the first embodiment of the present invention, at least one marker 60' is attached at a position spaced apart by a predetermined distance X (less than 100 cm) from the rotating shaft 56' on the upper flat surface of the rotor 50'. After the marker 60' has been attached as such, the gripper is moved in such a manner that the center of the sensor attached to the gripper or finger is placed on the circumference on which the marker 60' is located. Then, the position of the marker is detected while the final arm of the robot with the gripper attached thereto is caused to move in the predetermined rotating direction. Therefore, a correct position of a test tube located on an extension line passing through the centers of the rotating shaft 56' and marker 60' can be obtained. Consequently, the positions of other tubes can also be correctly obtained based on information on relative positions with respect to the detected tube position.

According to the present invention, although the microplates or test tubes are placed at arbitrary angular positions in the rotor of the centrifuge before or after the centrifugation, the angular positions thereof can be correctly detected by using the sensor and marker. Thus, desired microplates or test tubes can be easily and correctly mounted into and demounted from the centrifuge by using the gripper or fingers of the robot. Accordingly, all the centrifuging processes can be automatically performed even in any conventional centrifuges.

Further, since any sensors suitable for displacement or color measurement can be alternatively utilized and the marker can be attached onto any positions of the rotor of the centrifuge, the centrifugation can be automatically performed regardless of kinds and use environment of the centrifuges. Moreover, since the scanning of the marker by the sensor can be performed by means of the simple operation of moving the gripper in the predetermined rotating direction after moving the gripper so that the sensor attached to the gripper is placed onto the circumference of the circle where the marker is located, the overall operation of the automated centrifuge system is simplified. Therefore, the production costs of the automated centrifuge system can be remarkably reduced and reliability of the system can also be greatly improved.

While the invention has been shown and described with respect to the preferred embodiments, the present invention is not considered to be limited thereto. Further, it should be understood by the skilled in the art that various changes and modifications may be made thereto without departing from the spirit and scope of the invention as defined in the appended claims.

What is claimed is:

1. An automated centrifuge system for automatically centrifuging liquids containing biological materials such as nucleic acids in accordance with predetermined procedures, comprising:

a centrifuge including a rotor in which at least two swing buckets with at least two microplates mounted thereon are provided so as to perform centrifugation of the liquids, a multi-joint robot with at least three joints which includes a gripper attached to a final arm thereof and fingers attached to the gripper, and a controller for controlling the predetermined procedures and the operation of the robot, wherein the centrifuge and the multi-joint robot are disposed close to each other on a rigid bottom plate; a position detection sensor is attached to the gripper or one for fingers, at least one marker is attached at a predetermined position on a central frame of the rotor, said predetermined position being spaced apart from a rotating shaft of the rotor by a predetermined radial distance; and the controller causes the gripper to be moved so that the sensor is placed onto a circumference of a circle having a radius equal to the predetermined radial distance and the gripper to be moved around an axis of the rotating shaft of the rotor so that the sensor can detect a position of the marker, thereby automatically performing the predetermined procedures through the detection of positions of the microplates mounted to the swing buckets of the centrifuge.

2. The automated centrifuge system as claimed in claim 1, wherein the sensor is a laser displacement measurement sensor.

3. The automated centrifuge system as claimed in clam 1, wherein the sensor is an optical fiber sensor.

4. The automated centrifuge system as claimed in clam 1, wherein the predetermined radial distance is 100 cm or less.

5. The automated centrifuge system as claimed in claim 1, wherein the marker is made of a material having high corrosion resistance to water.

6. The automated centrifuge system as claimed in claim 5, wherein the material is one selected from the group consisting of aluminum and plastic.

7. The automated centrifuge system as claimed in claim 1, wherein at least two markers are disposed at an equiangular interval, which corresponds to a value of 360 degrees/number of markers, along the circumference of the circle having the predetermined radius on the frame of the rotor.

8. The automated centrifuge system as claimed in claim 7, wherein the markers have substantially same weight.

9. The automated centrifuge system as claimed in claim 7, wherein the markers have different shapes.

10. The automated centrifuge system as claimed in claim 7, wherein the markers have different colors.

11. An automated centrifuge system for automatically centrifuging liquids containing biological materials such as nucleic acids in accordance with predetermined procedures, comprising:

a centrifuge including a rotor in which a plurality of tube holes for receiving a plurality of test tubes with the liquids contained therein are formed at an equiangular interval on a circumference of a circle having a predetermined radius from a rotating shaft of the rotor, a multi-joint robot with at least three joints which includes a gripper attached to a final arm thereof and a finger attached to the gripper, and a controller for controlling the predetermined procedures and the operation of the robot, wherein the centrifuge and the multi-joint robot are disposed close to each other on a rigid bottom plate; a sensor for use in position detection is attached to the gripper or finger, at least one marker is attached at a predetermined position on a central frame of the rotor, said predetermined position being spaced apart from a rotating shaft by a predetermined radial distance smaller than the predetermined radius; and the controller causes the gripper to be moved so that the sensor is placed onto a circumference of a circle having a radius equal to the predetermined radial distance and the gripper to be moved around an axis of the rotating shaft of the rotor so that the sensor can detect a position of the marker, thereby automatically performing the predetermined procedures through the detection of positions of the respective test tubes inserted into the tube holes of the rotor of the centrifuge.

12. The automated centrifuge system as claimed in claim 11, wherein the sensor is a laser displacement measurement sensor.

13. The automated centrifuge system as claimed in clam 11, wherein the sensor is an optical fiber sensor.

14. The automated centrifuge system as claimed in clam 11, wherein the predetermined radial distance is 100 cm or less.

15. The automated centrifuge system as claimed in claim 11, wherein the marker is made of a material having high corrosion resistance to water.

16. The automated centrifuge system as claimed in claim 15, wherein the material is one selected from the group consisting of aluminum and plastic.

17. The automated centrifuge system as claimed in claim 11, wherein at least two markers are disposed at an equiangular interval, which corresponds to a value of 360 degrees/number of markers, along the circumference of the circle having the predetermined radius on the frame of the rotor.

18. The automated centrifuge system as claimed in claim 17, wherein the markers have substantially same weight.

19. The automated centrifuge system as claimed in claim 17, wherein the markers have different shapes.

20. The automated centrifuge system as claimed in claim 17, wherein the markers have different colors.

* * * * *